US005693337A

United States Patent [19]
Suzuki et al.

[11] Patent Number: 5,693,337
[45] Date of Patent: Dec. 2, 1997

[54] STABLE LIPID EMULSION

[75] Inventors: Hidekazu Suzuki; Satoshi Yamazaki; Yoshikazu Naito; Kenji Endo; Touru Oguma; Makoto Maeda, all of Tokyo, Japan

[73] Assignee: Wakamoto Pharmaceutical Co., Ltd., Tokyo, Japan

[21] Appl. No.: 500,087

[22] Filed: Jul. 10, 1995

[30] Foreign Application Priority Data

Jul. 13, 1994 [JP] Japan .................................. 6-183045

[51] Int. Cl.⁶ ............................................... A61K 9/127
[52] U.S. Cl. ............................ 424/450; 514/937; 514/943
[58] Field of Search ........................ 424/450; 514/937–943

[56] References Cited

U.S. PATENT DOCUMENTS

| 4,290,910 | 9/1981 | Harada | 252/312 |
| 4,970,209 | 11/1990 | Wretlind | 514/221 |

FOREIGN PATENT DOCUMENTS

| 55 056 | 12/1984 | Austria . |
| 0 220 152 | 4/1987 | European Pat. Off. . |
| 0 331 755 | 9/1989 | European Pat. Off. . |
| 0 599 543 | 6/1994 | European Pat. Off. . |
| 2 690 340 | 10/1993 | France . |
| 29 36 252 | 3/1980 | Germany . |
| 41 00 490 | 3/1992 | Germany . |
| 42 44 122 | 6/1994 | Germany . |
| 59-122423 | 7/1984 | Japan . |
| 64-56623 | 3/1989 | Japan . |
| 4-69340 | 3/1992 | Japan . |
| 4-264029 | 9/1992 | Japan . |
| 4-338334 | 11/1992 | Japan . |

OTHER PUBLICATIONS

Handbook of Oils and Fats Chemistry (edited by Nippon Oil Chemistry Association, published on Showa 33(1958), Jan. 25, pp. 658–659.

Handbook of Oils and Fats Chemistry (revised 3rd edition, edited by Nippon Oil Chemistry Association, Published on Heisei 1(1990), Feb. 28, pp. 76–77.

*Primary Examiner*—Gollamudi S. Kishore
*Attorney, Agent, or Firm*—Oblon, Spivak, McClelland, Maier & Neustadt, P.C.

[57] ABSTRACT

A lipid emulsion which comprises (A) an oil component, (B) an emulsifying agent containing yolk lecithin and/or soybean lecithin, and (C) water, wherein the lipid emulsion further comprises citric acid or a pharmaceutically acceptable salt thereof and at least one member selected from the group consisting of methionine, phenylalanine, serine, histidine and pharmaceutically acceptable salts thereof, provided that it does not simultaneously contain methionine and phenylalanine. The addition of citric acid and histidine, methionine, phenylalanine and/or serine to a lipid emulsion containing natural lecithin as an emulsifying agent permits the prevention of change of color and formation of oil drops associated with the conventional natural lecithin-containing lipid emulsion due to the synergistic effect of the foregoing additives. The drug-containing lipid emulsion is also excellent in storage stability and thus the foregoing lipid emulsion can be applied to drugs such as injections, eye drops, nasal drops, lotions or liniments, inhalants and drugs for oral administration or cosmetics such as humectants.

8 Claims, No Drawings

STABLE LIPID EMULSION

BACKGROUND OF THE INVENTION

The present invention relates to a lipid emulsion. More specifically, the present invention relates to a lipid emulsion, excellent in storage stability which comprises citric acid, and at least one member selected from the group consisting of methionine, phenylalanine, serine, and histidine as stabilizers.

The lipid emulsion is an oil in water (O/W) emulsion which comprises an oil component, a phospholipid-containing emulsifying agent and water. The lipid emulsion has been developed as a parenteral alimentation and has recently been studied and applied to various fields such as medicines and cosmetics. Since the lipid emulsion contains, in particular, a phospholipid as an emulsifying agent, it is highly safe, suitable for stabilizing drugs which are unstable in aqueous solutions, for sustained release of drugs and for targeting of drugs to lesion site and there have presently been put on the market several kinds of lipid emulsions comprising drugs, while making use of these characteristic properties. For instance, Intralipos (registered trade mark) 10% [comprising 1.2% purified yolk lecithin and 10% soybean oil; available from The Green Cross Corporation] and Intralipos (registered trade mark) 20% [comprising 1.2% purified yolk lecithin and 20% soybean oil; available from The Green Cross Corporation] have been put on the market as lipid emulsions for parenteral alimentation. Moreover, there have been put on the market, as drug-containing lipid emulsions, Limethason (registered trade mark) [comprising 0.4% dexamethasone palmitate, 1.2% purified yolk lecithin and 10% soybean oil; available from The Green Cross Corporation] and Lipfen (registered trade mark) [comprising 1% flurbiprofen axetil, 1.2% purified yolk lecithin and 10% soybean oil; available from The Green Cross Corporation].

However, the majority of lipid emulsions are unstable to heat and there has been known that when they are stored, they suffer from problems such as an increase in the particle size, formation of oil drops, a reduction of pH and change of color. The same is also true for the lipid emulsions which are already put on the market and they are inferior in the storage stability to other pharmaceutical preparations of drugs. It is thus one of important problems when developing a lipid emulsion capable of being put on the market to improve the storage stability of the emulsion.

Some attempts have been done to improve the storage stability of the lipid emulsion. The indices for the stability, in particular, apparent change of color which can most easily be recognized is mainly caused due to the presence of degradation products formed through oxidation of phospholipids used in the lipid emulsion as emulsifying agents. In respect of preventing oxidation of lipids, various kinds of antioxidants (such as phenolic compounds, amino acids and terpenes) are disclosed in a Handbook of Oils and Fats Chemistry (revised 3rd edition, edited by Nippon Oil Chemistry Association, published on Heisei 2 (1990), February 28, pp. 76–77). Moreover, a Handbook of Oils and Fats Chemistry (edited by Nippon Oil Chemistry Association, published on Showa 33 (1958), January 25, p. 658) discloses compounds which are free of anti-oxidant action but can enhance the anti-oxidant activity of other antioxidants, i.e., synergists (such as citric acid, malonic acid and pyruvic acid). However, all of these antioxidants or synergists do not always show excellent antioxidant effect in the lipid emulsion of the present invention so far as the experiments carried out by the inventors of this invention are concerned.

In addition, as a means for preventing the oxidation of the phospholipids, Japanese Un-examined Patent Publication (hereinafter referred to as "J.P. KOKAI") No. Sho 59-122423 discloses a method which comprises adding vitamin E to the lipid emulsion as an antioxidant. However, vitamin E per se is unstable to heat and light rays and accordingly, the lipid emulsion suffers from a problem of causing change of color due to the decomposition of vitamin E.

Moreover, J.P. KOKAI No. Hei 4-264029 discloses the simultaneous use of EDTA as a chelating agent and citric acid as a pH-adjusting agent for the improvement of the stability of the lipid emulsion, but EDTA is insufficient in safety and the use thereof as an additive for pharmaceutical preparation is thus restricted.

In addition, J.P. KOKAI Nos. Hei 4-69340, Hei 4-264029 and Hei 4-338334 disclose methods for improving the stability of the lipid emulsion which comprises adding citric acid and salts thereof to the emulsion as antioxidants.

SUMMARY OF THE INVENTION

Accordingly, an object of the present invention is to provide a lipid emulsion excellent in storage stability which comprises citric acid, and at least one member selected from the group consisting of methionine, phenylalanine, serine, and histidine as stabilizers.

The inventors of this invention have conducted intensive studies to develop a lipid emulsion having good storage stability using, as an emulsifying agent, a natural phospholipid which is safe and cheaper than synthetic or semisynthetic phospholipid. As a result, the inventors have found out that the simultaneous use of citric acid or salts thereof as a synergist and a specific amino acid as an antioxidant in a lipid emulsion permits marked improvement in the storage stability as compared with that achieved through the simultaneous use of other synergists and other antioxidants, i.e., permits the prevention of change of color of the lipid emulsion and/or the formation of oil drops due to the destruction of the emulsion during storage thereof and hence permits the preparation of a lipid emulsion excellent in storage stability. Moreover, the inventors have also found out that the same effect can be expected even when the foregoing components are simultaneously used in a lipid emulsion containing a drug. The inventors have thus completed the present invention on the basis of the foregoing findings.

According to the present invention, there is thus provided a lipid emulsion which comprises (A) an oil component, (B) an emulsifying agent containing yolk lecithin and/or soybean lecithin and (C) water, wherein the lipid emulsion further comprises citric acid or a pharmaceutically acceptable salt thereof and at least one member selected from the group consisting of methionine, phenylalanine, serine, histidine and pharmaceutically acceptable salts thereof, provided that the lipid emulsion does not simultaneously contain methionine and phenylalanine.

DESCRIPTION OF THE PREFERRED EMBODIMENTS

The present invention will be described in more detail below.

In the present invention, the "emulsifying agent" may be, for instance, yolk lecithin and soybean lecithin. Therefore, the emulsifying agent is not restricted to specific ones so far as they have compositions which comprise the foregoing lecithin and the intended effect of the present invention can also be expected if lyso-forms of these lecithins or hydrogenated forms thereof or dimyristoylphosphatidylcholine, dipalmitoylphosphatidylcholine and distearoylphosphatidyl-choline which are synthetic phospholipids are used with yolk lecithin and/or soybean lecithin. Moreover, the intended effect of the present invention can likewise be expected if phospholipids other than those listed above such as phosphatidylethanolamine or the lyso-form thereof, phosphatidylserine, phosphatidylinositol, dicetylphosphate, sphingomyelin are used with yolk lecithin and/or soybean lecithin.

In preparing the lipid emulsion of the present invention, the amount of these emulsifying agents to be used is not particularly restricted, but preferably ranges from 1/50 to 3 parts by weight and more preferably 1/30 to 2 parts by weight per one part by weight of the oil component.

In addition, an auxiliary agent for emulsification may, if desired, be added to these emulsifying agents. Examples of such auxiliary agents for emulsification include phosphatidic acid, sterols such as cholesterols, aliphatic amines such as stearylamine, and fatty acids or pharmaceutically acceptable salts thereof such as oleic acid, stearic acid, linoleic acid, palmitic acid, linolenic acid and myristic acid. Examples of pharmaceutically acceptable salts of fatty acids include sodium and potassium salts. The amount of these auxiliary agent for emulsification to be used is not restricted to a specific range, but is in general not more than 0.2 part by weight for sterols and not more than 0.5 part by weight for phosphatidic acid, aliphatic amines or fatty acids, per one part by weight of the emulsifying agent.

The citric acid used in the present invention as a stabilizer may be citric acid or pharmaceutically acceptable salts thereof. Examples of the pharmaceutically acceptable salts of citric acid include sodium citrate (trisodium citrate dihydrate), sodium dihydrogen citrate, disodium hydrogen citrate or hydrates thereof, trisodium citrate, potassium dihydrogen citrate, dipotassium hydrogen citrate and tripotassium citrate.

The amino acid used in the present invention as a stabilizers may be at least one member selected from the group consisting of methionine, phenylalanine, serine and histidine or pharmaceutically acceptable salts thereof. The pharmaceutically acceptable salts of histidine may be, for instance, hydrochloride salt.

It is an essential requirement in the present invention to simultaneously use citric acid and at least one of the foregoing amino acids. The use of amino acids othere than those listed above never permits achievement of the intended effect of the present invention and the effect cannot be accomplished by the use of compounds (such as malonic acid and pyruvic acid) known as the synergists for antioxidants other than citric acid. In addition, the intended effect of the present invention cannot be achieved by the simultaneous use of phenylalanine and methionine and accordingly, the combination is not preferred.

Moreover, the range of the mixing rate of these stabilizers which can ensure the intended effect of the present invention slightly varies depending on the kind of the amino acid used in combination with citric acid.

For instance, if citric acid or its pharmaceutically acceptable salt and histidine or its pharmaceutically acceptable salt are used in combination, the amount of citric acid or the pharmaceutically acceptable salt is in the range of 0.01 to 0.27 part by weight, preferably 0.05 to 0.27 part by weight, per one part by weight of emulsifying agent, with the proviso that the amount of the salt is expressed in terms of citric acid, and the amount of histidine or the pharmaceutically acceptable salt is in the range of 0.008 to 0.83 part by weight, preferably 0.03 to 0.17 part by weight, per one part by weight of emulsifying agent, with the proviso that the amount of the salt is expressed in terms of histidine.

Moreover, if citric acid or its pharmaceutically acceptable salt and methionine or its pharmaceutically acceptable salt are used in combination, the amount of citric acid or the pharmaceutically acceptable salt is in the range of 0.027 to 0.27 part by weight, preferably 0.05 to 0.27 part by weight, per one part by weight of emulsifying agent, with the proviso that the amount of the salt is expressed in terms of citric acid, and the amount of methionine or the pharmaceutically acceptable salt is in the range of 0.08 to 1.7 part by weight, preferably 0.17 to 1.7 part by weight, per one part by weight of emulsifying agent, with the proviso that the amount of the salt is expressed in terms of methionine.

Further, if citric acid or its pharmaceutically acceptable salt and phenylalanine or its pharmaceutically acceptable salt are used in combination, the amount of citric acid or the pharmaceutically acceptable salt is in the range of 0.05 to 0.22 part by weight, preferably 0.08 to 0.22 part by weight, per one part by weight of emulsifying agent, with the proviso that the amount of the salt is expressed in terms of citric acid, and the amount of phenylalanine or the pharmaceutically acceptable salt is in the range of 0.4 to 0.83 part by weight, preferably 0.5 to 0.83 part by weight, per one part by weight of emulsifying agent, with the proviso that the amount of the salt is expressed in terms of phenylalanine.

In addition, if citric acid or its pharmaceutically acceptable salt and serine or its pharmaceutically acceptable salt are used in combination, the amount of citric acid or the pharmaceutically acceptable salt is in the range of 0.03 to 0.27 part by weight, preferably 0.03 to 0.22 part by weight, per one part by weight of emulsifying agent, with the proviso that the amount of the salt is expressed in terms of citric acid, and the amount of serine or the pharmaceutically acceptable salt is in the range of 0.16 to 2.9 part by weight, preferably 0.5 to 1.7 part by weight, per one part by weight of emulsifying agent, with the proviso that the amount of the salt is expressed in terms of serine.

The intended effect of the present invention can be ensured through the simultaneous use of citric acid and amino acid in the mixing rate defined above relative to the amount of the emulsifying agent. However, if the amount of citric acid exceeds a predetermined level, the emulsion is destructed and this results in the formation of oil drops. Therefore, it is preferred to use citric acid or its pharmaceutically acceptable salt in an amount of not more than 0.0016 part by weight per one part by weight of the lipid emulsion, with the proviso that the amount of the salt is expressed in terms of citric acid.

The "oil component" used in the present invention may be, for instance, vagetable oils and/or synthetic or semisynthetic glycerides. Examples of vegetable oils are soybean oil, sesame oil, cottonseed oil, rapeseed oil, orange oil, corn oil and olive oil. The synthetic or semisynthetic glyceride is not restricted to specific ones, but examples thereof in general include mono-, di- or triglycerides whose acid components are $C_6$ to $C_{20}$ saturated and/or unsaturated fatty acids and mixtures comprising at least two members of these glycerides.

In the preparation of the lipid emulsion of the present invention, the amount of these oil components is not particularly restricted, but preferably ranges from 0.1 to 50% and more preferably 0.5 to 30%.

The drugs which may be added to the lipid emulsion of the present invention are not particularly restricted, but preferably those exhibiting strong affinity for the oil component or the emulsifying agent. Examples thereof are agents affecting central nervous system, agents affecting peripheral nervous system, agents for ophthalmic use, cardiovascular agents, agents affecting respiratory organs, agents affecting digestive organs, hormone preparations, vitamin preparations, agents related to blood and body fluids, agents affecting metabolism, antineoplastic agents, antiallergic agents, antibiotic preparations, chemotherapeutics, diagnostic agents, alkaloidal narcotics and immunoregulatory drugs. Specific examples of these drugs will be detailed below, but the present invention is not restricted to these specific ones.

(1) Agents affecting central nervous system, for instance,
   a) hypnotics and sedatives and antianxiety agents such as diazepam, nitrazepam and phenobarbital;
   b) antiepileptics such as carbamazepine or derivatives thereof, diazepam, phenytoin, primidone and phenobarbital;
   c) antipyretics, analgesics and antiinflammatories such as acetaminophen, flurbiprofen or derivatives thereof, ibuprofen or derivatives thereof, indometacin or derivatives thereof, ketoprofen or derivatives thereof, diclofenac or derivatives thereof, pranoprofen or derivatives thereof and glycyrrhetic acid;
   d) antidepressants and tranquilizers such as imipramine or derivatives thereof and sulpiride;

(2) Agents affecting peripheral nervous system, for instance,
   a) local anesthetics such as dibucaine, procaine, lidocaine or derivatives of these drugs;
   b) sympatholytics such as tolazoline;
   c) antispasmodics such as afloqualone, flopropione, eperisone, papaverine or derivatives thereof and dicycloverine;

(3) Agents for ophthalmic use, for instance,
   a) antiglaucoma drugs such as epinephrine, Timolol, carteolol, or derivatives thereof;
   b) anticataract drugs such as pirenoxine or derivatives thereof;
   c) mydriatics such as tropicamide;
   d) miotics such as pilocarpine or derivatives thereof;

(4) Cardiovascular agents, for instance,
   a) cardiotonics such as denopamine or derivatives thereof, etilefrine, digoxin and ubidecarenone;
   b) antiarrhythmic agents such as atenolol, carteolol, propranolol or derivatives thereof, verapamil and pindolol;
   c) diuretics such as furosemide;
   d) antihypertensives such as diltiazem, celiprolol, nicardipine, propranolol, prazosin, manidipine, captopril or derivatives thereof and enalapril;
   e) vasoconstrictors such as naphazoline, phenylephrine, methoxamine or derivatives thereof and dihydroergotamine;
   f) vasodilators such as nicardipine, barnidipine, isosorbide and nifedipine;
   g) antihyperlipemia agents such as clofibrate or derivatives thereof, pravastatin, simvastatin and probucol or derivatives thereof;

(5) Agents affecting respiratory organs, for instance,
   a) antitussives such as cloperastine, methylephedrine, dextromethorphan, noscapine and dimemorfan;
   b) bronchodilators such as procaterol, theophylline or derivatives thereof and salbutamol;

(6) Agents affecting digestive organs, for instance,
   a) agents for peptic ulcers such as aldioxa, omeprazole, cimetidine and famotidine;
   b) gastroprokimetics such as trimebutine and cisapride;

(7) Hormones, for instance,
   a) adrenal hormone preparations such as epinephrine, hydrocortisone, prednisolone, cortisone, betamethasone, dexametasone, triamcinolone, beclometasone, fluorometholone, clobetasone, or derivatives thereof;
   b) prostaglandin agents such as prostaglandin $E_1$, prostaglandin $E_2$, prostaglandin $F_2$, prostaglandin $I_2$, or derivatives thereof;

(8) Vitamins such as vitamin A, vitamin D, vitamin E, vitamin K, or derivatives thereof;

(9) Agents related to blood and body fluids, for instance,
   a) hemostatics such as carbazochrome or derivatives thereof, and polidocanol;

(10) Agents affecting metabolism, for instance,
   a) agents for treatment of gout such as allopurinol or derivatives thereof, colchicine or derivatives thereof and probenecid;
   b) antidiabetics such as glibenclamide and tolbutamide or derivatives thereof;
   c) aldose reductase inhibitors such as epalrestat and [5-(3-thienyl)-1H-tetrazol-1-yl] acetic acid;

(11) Antineoplastics such as tegafur, fluorouracil, methotrexate, doxorubicin, mitomycin C, tamoxifen, cisplatin, adriamycin, vincristine, or derivatives thereof;

(12) Antiallergic agents such as diphenhydramine or derivatives thereof, promethazine or derivatives thereof, clemastine or derivatives thereof, chlorpheniramine or derivatives thereof, mequitazine, glycyrrhizin or derivatives thereof, tazanolast, tranilast or derivatives thereof, ketotifen or derivatives thereof and 3'-(1H-tetrazol-5-yl) oxanilic acid;

(13) Antibiotics such as amphotericin B, erythromycin, tetracycline, chloramphenicol, cefixime, miconazole, pimaricin, or derivatives of these drugs;

(14) Chemotherapeutics, for instance,
   a) synthetic antibacterials such as norfloxacin or derivatives thereof, ofloxacin or derivatives thereof, sparfloxacin and levofloxacin;
   b) antivirals such as aciclovir or derivatives thereof;

(15) Diagnostic agents, for instance,
   a) X-ray contrast agents such as propyliodone;
   b) reagents for various function tests such as amogastrin;
   c) diagnostic agents such as fluorescein or derivatives thereof;

(16) Alkaloidal narcotics such as morphine or derivatives thereof, codeine or derivatives thereof and cocaine;

(17) Immunoregulatory drugs such as azathioprine and ciclosporin or derivatives thereof.

The method for preparing the lipid emulsion of the present invention will hereinafter be described in detail. Various known methods may be used. For instance, yolk lecithin and, if desired, phospholipids such as yolk phosphatidylethanolamine and auxiliary agents for emulsification such as oleic acid are dissolved in an appropriate organic solvent such as hexane and then the solvent is distilled off under reduced pressure to give a lipid film. To the resulting lipid film, there are added an oil component and water and the mixture is preliminarily emulsified by vigorously stirring through shaking. The resulting liquid is emulsified using the currently used emulsifier. After completion of the emulsification, the pH value of the resulting emulsion is adjusted to a predetermined level by addition of HCl or NaOH. Then citric acid and amino acids are added to the emulsion to give a lipid emulsion of the present invention. Alternatively, the lipid emulsion of the present invention can likewise be prepared by adding an oil component and an aqueous solution of citric acid and amino acids to the lipid film prepared by the foregoing procedures and then subjecting the resulting mixture to the emulsification procedures.

Moreover, the preparation of a lipid emulsion containing a drug according to the present invention can be prepared by adding a drug together with an oil component and water or an aqueous solution of a stabilizer, followed by the same procedures used above. Alternatively, a drug is added to an organic solvent together with an emulsifying agent and, if desired, an auxiliary agent for emulsification, followed by the same procedures used above. Moreover, the drug remaining in the aqueous solution moiety of the lipid emulsion can be, if desired, removed by, for instance, the gel filtration, centrifugation or affinity chromatography.

The lipid emulsion of the present invention thus prepared may be applied to various fields. For instance, the emulsion can be used in pharmaceutical preparation in the form of an injection, an eye drop, a nasal drop, a lotion, a liniment, an inhalant and a drug for oral administration. In addition, it can also be used in cosmetics, i.e., it can be processed into a humectant for the care or repair of the skin.

When the lipid emulsion of the present invention is processed into preparations such as those discussed above, it is possible to add, to the preparations, isotonic agents such as saccharides or glycerin; pH-adjusting agents; antiseptic agents such as methyl p-hydroxybenzoate and propyl p-hydroxybenzoate; thickening agents such as methyl cellulose, polyvinyl pyrrolidone or sodium polyacrylate; and/or stabilizers such as albumin, dextran, polyethylene glycol or gelatin, in such an amount that the intended effect of the present invention is not impaired.

Moreover, the lipid emulsion of the present invention may be subjected to a sterilization treatment such as the sterilization in an autoclave or the fractional sterilization.

Then the present invention will hereunder be described in more detail with reference to the following Examples, but the present invention is not restricted to these Examples.

Evaluation of Storage Stability

The stability of the lipid emulsion was evaluated by examining the stability thereof to heat. The thermal stability of articles has generally been investigated to evaluate the long-term storage stability thereof. The thermal stability was evaluated by determining changes in appearance. More specifically, it was evaluated by observing whether oil drops were formed or not and by determining the degree of change of color.

When the lipid emulsion becomes unstable, it is observed that the emulsion causes change of color from milk white to yellow. To express the degrees of change of color by numerical values, the color difference (ΔE) between each sample before and after storage was determined using a color difference meter (Model ND-504DE available from Nippon Denshoku Kogyo Co., Ltd.). Coordinate values based on the USC system of color representation, L, a and b, were measured by the color difference meter with respect to the same sample before and after the storage, and the values of ΔE were calculated in accordance with the following equation:

$$\Delta E = [(L_1 - L_2)^2 + (a_1 - a_2)^2 + (b_1 - b_2)^2]^{1/2}$$

wherein $L_1$, $a_1$ an $b_1$ are the values of the sample measured before the storage while $L_2$, $a_2$ and $b_2$ are the values of the sample measured after the storage.

The color difference has widely been used in various fields as one of indices for the quality control of various articles.

It has generally been said that if the color difference (ΔE) exceeds 3, the change of color can clearly be recognized with the naked eyes. For this reason, a sample exhibiting the color difference of less than 2.50 was evaluated to be "no change of color" and further, when the color difference is no less than 2.50, it was divided into three groups on the basis of the following evaluation criteria:

no change in color: ΔE<2.50(milk white when observed with naked eyes)

*: 2.50≦ΔE<4.00(pale yellow when observed with naked eyes)

**: 4.00≦ΔE<6.00(yellow when observed with naked eyes)

***: 6.00≦ΔE (yellowish brown when observed with naked eyes)

In addition, when the emulsified system becomes unstable and the emulsion is destroyed, the formation of oil drops is observed. The fact that a sample forms oil drops after the storage is indicated as "oil drops".

EXAMPLE 1

To one volume of a commercially available yolk lecithin-containing lipid emulsion (Intralipos® 10%), there was added one volume of a 2% glycerin aqueous solution containing sodium citrate and one or more member selected from histidine, methionine, phenylalanine and serine and whose pH value was adjusted to 7.0 to give a lipid emulsion according to the present invention. By way of comparison, to one volume of Intralipos® 10%, there was added one volume each of the following solution:

(a) a 2% glycerin aqueous solution containing sodium citrate and whose pH value was adjusted to 7.0;

(b) a 2% glycerin aqueous solution containing one or more member selected from the amino acids listed above and whose pH value was adjusted to 7.0;

(c) a 2% glycerin aqueous solution whose pH was adjusted to 7.0;

(d) a 2% glycerin aqueous solution containing sodium citrate and an amino acid other than those used in the present invention and whose pH value was adjusted to 7.0;

(e) a 2% glycerin aqueous solution containing sodium citrate and a water-soluble antioxidant and whose pH value was adjusted to 7.0; or (f) a 2% glycerin aqueous solution containing methionine and a synergist other than citric acid and whose pH value was adjusted to 7.0; to give a comparative lipid emulsion.

Each lipid emulsion prepared above (0.5 ml each) was charged into a 1 ml volume ampoule and then the ampoule was sealed. Thereafter, the ampoule was stored at 60° C. to inspect it for the change in appearance. The change in appearance of each sample was observed after storing over 3 weeks. The results thus obtained are summarized in the following Table 1. The comparative lipid emulsions to which the foregoing stabilizers (a) to (f) caused change of color or formation of oil drops. Moreover, change of color was likewise observed when the sample simultaneously containing citric acid, phenylalanine and methionine. Contrary to this, the lipid emulsions of the present invention did not cause any change of color or formation of oil drops. This clearly indicates that the lipid emulsion of the present invention is stable.

TABLE 1

Example 1

| Stabilizer (part by weight)[1] | | Appearance[2] | |
|---|---|---|---|
| Citric Acid | | Change of Color[3] | Form-ation of oil Drops |
| | Amino Acid | | |
| *Present Invention* | | | |
| 0.055 | histidine (0.017) | NCC (2.49) | |
| 0.11 | histidine (0.83) | NCC (1.95) | |
| 0.055 | methionine (0.17) | NCC (2.34) | |
| 0.11 | methionine (0.83) | NCC (2.37) | |
| 0.055 | phenylalanine (0.42) | NCC (2.48) | |
| 0.11 | phenylalanine (0.83) | NCC (2.45) | |
| 0.055 | serine (0.17) | NCC (2.05) | |
| 0.11 | serine (0.83) | NCC (2.26) | |
| 0.055 | his(0.017) + phe(0.42) | NCC (1.95) | |
| 0.055 | his(0.017) + met(0.17) | NCC (2.13) | |
| 0.055 | his(0.017) + ser(0.17) | NCC (1.81) | |
| 0.055 | phe(0.42) + ser(0.17) | NCC (2.14) | |
| 0.055 | met(0.17) + ser(0.17) | NCC (2.22) | |
| 0.055 | his(0.017) + phe(0.42) + ser(0.17) | NCC (1.85) | |
| 0.055 | his(0.017) + met(0.17) + ser(0.17) | NCC (2.15) | |
| *Comp. Ex.* | | | |
| — | — | ***(7.27) | oil drop |
| 0.22 | — | * (3.39) | |
| 0.11 | — | * (3.41) | |
| 0.06 | — | * (3.74) | |
| 0.03 | — | * (3.98) | |
| — | histidine (0.034) | ** (5.84) | |
| — | histidine (1.67) | ***(8.33) | |
| — | methionine (0.34) | ** (5.85) | |
| — | methionine (1.67) | *** (6.12) | |
| — | phenylalanine (0.84) | ** (5.96) | |
| — | phenylalanine (1.67) | *** (6.60) | |
| — | serine (0.34) | ** (5.95) | |
| — | serine (1.67) | *** (6.45) | |
| — | his(0.034) + phe(0.84) | ** (4.77) | |
| — | his(0.034) + met(0.34) | ** (4.61) | |
| — | his(0.034) + ser(0.34) | ** (5.32) | |
| — | phe(0.84) + ser(0.34) | ** (4.91) | |
| — | met(0.34) + ser(0.34) | ** (4.97) | |
| — | his(0.034) + phe(0.84) + ser(0.34) | ** (4.13) | |
| — | his(0.034) + met(0.34) + ser(0.34) | ** (4.64) | |
| — | his(0.034) + phe(0.84) + met(0.34) | ** (4.00) | |
| — | phe(0.84) + met(0.34) + ser(0.34) | * (3.71) | |
| 0.055 | phe(0.42) + met(0.17) | * (2.60) | |
| 0.055 | his(0.017) + phe(0.42) + met(0.17) | * (2.53) | |
| 0.055 | phe(0.42) + met(0.17) + ser(0.17) | * (2.62) | |
| 0.055 | leutine (0.33) | * (3.67) | |
| 0.11 | leucine (0.83) | * (3.41) | |
| 0.055 | isoleucine (0.33) | * (3.63) | |
| 0.11 | isoleucine (0.83) | * (3.42) | |
| 0.055 | threonine (0.33) | * (3.39) | |
| 0.11 | threonine (0.83) | * (3.05) | |
| 0.055 | valine (0.33) | * (3.70) | |
| 0.11 | valine (0.83) | ** (4.77) | |
| 0.055 | tryptophan (0.17) | ** (5.82) | |

TABLE 1-continued

Example 1

| Stabilizer (part by weight)[1] | | Appearance[2] | |
|---|---|---|---|
| Citric Acid | | Change of Color[3] | Form-ation of oil Drops |
| 0.11 | tryptophan (0.83) | *** (13.26) | |
| 0.03 | arginine (0.15) | * (2.77) | |
| 0.11 | arginine (0.83) | ** (5.34) | oil drop |
| 0.03 | lysine (0.05) | * (3.35) | |
| 0.11 | lysine (0.83) | ** (5.27) | oil drop |
| 0.11 | glutamic acid (0.1) | * (3.20) | |
| 0.11 | glutamic acid (0.83) | * (3.01) | |
| 0.11 | Aspartic acid (0.83) | * (3.28) | |
| 0.03 | glycine (0.15) | * (3.59) | |
| 0.11 | glycine (0.83) | * (3.04) | |
| 0.11 | proline (0.05) | * (3.21) | |
| 0.11 | proline (0.83) | ** (4.30) | |
| 0.11 | cysteine (0.1) | * (3.97) | |
| 0.11 | cysteine (0.83) | ** (5.76) | |
| | Water-Soluble Antioxidant | | |
| *Comp. Ex.* | | | |
| 0.11 | thioglycolic acid (0.83) | *** (10.49) | |
| 0.11 | ascorbic acid (0.83) | *** (7.53) | |
| 0.11 | sodium sulfite (0.83) | *** (11.60) | |
| 0.11 | sodium hydrogen sulfite (0.83) | *** (10.98) | |
| 0.11 | sorbitol (0.83) | ** (4.31) | |
| *Comp. Ex.* | | | |
| pyruvic acid(0.055) + met(0.17) | | *** (7.91) | |
| fumaric acid(0.055) + met(0.17) | | *** (7.82) | |
| malonic acid(0.055) + met(0.17) | | *** (7.34) | |
| maleic acid (0.055) + met(0.17) | | *** (7.26) | |
| ascorbic acid(0.055) + met(0.17) | | *** (9.08) | |
| succinic acid(0.055) + met(0.17) | | *** (7.89) | |
| phosphoric acid(0.055) + met(0.17) | | *** (8.17) | |

[1]The amount of the stabilizer to be added is expressed in terms of part by weight per one part by weight of the emulsifying agent, with the proviso that the amount of sodium citrate is expressed in terms of the amount of citric acid. his: histidine; ser: serine; phe: phenylalanine; met: methionine
[2]This means the change in appearance observed after storing at 60° C. for three weeks.
[3]"NCC" means "no change of color". Each numerical value in the parenthesis indicates the corresponding value of ΔE.

EXAMPLE 2

To one volume of a commercially available yolk lecithin-containing lipid emulsion (Intralipos® 10%), there was added one volume of a 2% glycerin aqueous solution containing sodium citrate and histidine, methionine, phenylalanine or serine in various concentrations as shown in Table 2 and whose pH was adjusted to 7.0. By way of comparison, to one volume of Intralipos 10%, there was added one volume of a 2% glycerin aqueous solution containing either sodium sitrate or the foregoing amino acid and whose pH was adjusted to 7.0 or a 2% aqueous glycerin solution whose pH was adjusted to 7.0 to give each corresponding comparative lipid emulsion.

Each lipid emulsion prepared by the foregoing procedures was stored at 60° C. and then inspected for the change in appearance in the same manner used in Example 1. The change in the appearance of each sample was observed after storing over 3 weeks. The results thus obtained are summarized in the following Table 2. These results indicate that the intended effect of the present invention can be achieved by simultaneous addition of citric acid and histidine, methionine, phenylalanine and/or serine in the mixing ratio detailed below, with respect to one part by weight of the emulsifying agent.

(a) 0.01 to 0.27 part by weight of citric acid and 0.008 to 0.83 part by weight of histidine;

(b) 0.027 to 0.27 part by weight of citric acid and 0.08 to 1.7 part by weight of methionine;

(c) 0.05 to 0.22 part by weight of citric acid and 0.4 to 0.83 part by weight of phenylalanine;

(d) 0.03 to 0.27 part by weight of citric acid and 0.16 to 2.9 parts by weight of serine.

TABLE 2

Example 2

| Stabilizer (parts by weight)[1] | | Appearance[2] | |
|---|---|---|---|
| Citric Acid | Amino Acid | Change of Color[3] | Formation of oil Drops |
| Present Invention | | | |
| 0.27 (0.0016) | histidine: 0.17 | NCC(2.33) | |
| 0.27 (0.0016) | histidine: 0.03 | NCC(2.42) | |
| 0.11 (0.00066) | histidine: 0.83 | NCC(2.37) | |
| 0.11 (0.00066) | histidine: 0.008 | NCC(2.42) | |
| 0.11 (0.00066) | histidine: 0.17 | NCC(1.98) | |
| 0.11 (0.00066) | histidine: 0.03 | NCC(2.49) | |
| 0.05 (0.0003) | histidine: 0.17 | NCC(2.12) | |
| 0.05 (0.0003) | histidine: 0.08 | NCC(2.11) | |
| 0.05 (0.0003) | histidine: 0.03 | NCC(2.41) | |
| 0.027 (0.00016) | histidine: 0.08 | NCC(2.46) | |
| 0.01 (0.00006) | histidine: 0.08 | NCC(2.40) | |
| Comp. Ex. | | | |
| 0.33 (0.0020) | histidine: 0.17 | NCC(2.35) | oil drop |
| 0.33 (0.0020) | histidine: 0.03 | NCC(2.46) | oil drop |
| 0.11 (0.00066) | histidine: 1.67 | * (2.64) | |
| 0.11 (0.00066) | histidine: 0.004 | * (2.80) | |
| 0.005 (0.00003) | histidine: 0.83 | *** (6.13) | |
| 0.005 (0.00003) | histidine: 0.008 | ** (4.47) | |
| 0.005 (0.00003) | histidine: 0.08 | * (3.56) | |
| 0.54 (0.0032) | — | * (3.75) | oil drop |
| 0.22 (0.0013) | — | * (3.39) | |
| 0.11 (0.00066) | — | * (3.41) | |
| 0.02 (0.00012) | — | ** (4.42) | |
| — | histidine: 1.66 | *** (8.33) | |
| — | histidine: 0.34 | ** (5.70) | |
| — | histidine: 0.16 | ** (5.64) | |
| — | histidine: 0.016 | *** (6.24) | |
| — | — | *** (7.27) | oil drop |
| Present Invention | | | |
| 0.27 (0.0016) | methionine: 0.17 | NCC(2.35) | |
| 0.27 (0.0016) | methionine: 1.7 | NCC(2.36) | |
| 0.27 (0.0016) | methionine: 0.42 | NCC(2.41) | |
| 0.11 (0.00066) | methionine: 1.7 | NCC(2.31) | |
| 0.11 (0.00066) | methionine: 0.08 | NCC(2.32) | |
| 0.05 (0.0003) | methionine: 1.7* | NCC(2.34) | |
| 0.05 (0.0003) | methionine: 0.42 | NCC(2.46) | |
| 0.05 (0.0003) | methionine: 0.08 | NCC(2.46) | |
| 0.027 (0.00016) | methionine: 1.7 | NCC(2.40) | |
| Comp. Ex. | | | |
| 0.33 (0.0020) | methionine: 1.7 | NCC(2.34) | oil drop |
| 0.33 (0.0020) | methionine: 0.42 | NCC(2.42) | oil drop |
| 0.11 (0.00066) | methionine: 0.02 | * (2.50) | |
| 0.01 (0.00006) | methionine: 1.7 | * (2.75) | |
| 0.01 (0.00006) | methionine: 0.08 | ** (4.98) | |
| 0.54 (0.0032) | — | * (3.75) | oil drop |
| 0.22 (0.0013) | — | * (3.39) | |
| 0.11 (0.00066) | — | * (3.41) | |
| 0.054 (0.00032) | — | * (3.51) | |
| — | methionine: 3.4 | ** (4.23) | |

TABLE 2-continued

Example 2

| Stabilizer (parts by weight)[1] | | Appearance[2] | |
|---|---|---|---|
| Citric Acid | Amino Acid | Change of Color[3] | Formation of oil Drops |
| — | methionine: 0.34 | *** (8.05) | |
| — | methionine: 0.16 | *** (7.92) | |
| — | — | *** (7.27) | oil drop |
| Present Invention | | | |
| 0.22 (0.0013) | phenylalanine: 0.83 | NCC(2.46) | |
| 0.22 (0.0013) | phenylalanine: 0.5 | NCC(2.48) | |
| 0.11 (0.00066) | phenylalanine: 0.83 | NCC(2.45) | |
| 0.11 (0.00066) | phenylalanine: 0.4 | NCC(2.39) | |
| 0.08 (0.00048) | phenylalanine: 0.83 | NCC(2.40) | |
| 0.08 (0.00048) | phenylalanine: 0.4 | NCC(2.48) | |
| 0.08 (0.00048) | phenylalanine: 0.5 | NCC(2.44) | |
| 0.05 (0.0003) | phenylalanine: 0.83 | NCC(2.41) | |
| Comp. Ex. | | | |
| 0.27 (0.0016) | phenylalanine: 0.83 | * (2.60) | |
| 0.11 (0.00066) | phenylalanine: 0.17 | * (2.80) | |
| 0.027 (0.00016) | phenylalanine: 0.83 | * (2.73) | |
| 0.44 (0.0026) | — | * (3.56) | oil drop |
| 0.22 (0.0013) | — | * (3.39) | |
| 0.16 (0.0009) | — | * (3.44) | |
| 0.11 (0.00066) | — | * (3.41) | |
| — | phenylalanine: 1.66 | *** (6.60) | |
| — | phenylalanine: 0.84 | *** (7.57) | |
| — | — | *** (7.27) | oil drop |
| Present Invention | | | |
| 0.27 (0.0016) | serine: 0.83 | NCC(2.40) | |
| 0.22 (0.0013) | serine: 1.7 | NCC(2.35) | |
| 0.22 (0.0013) | serine: 2.9 | NCC(2.47) | |
| 0.22 (0.0013) | serine: 0.5 | NCC(2.39) | |
| 0.11 (0.00066) | serine: 1.7 | NCC(2.34) | |
| 0.05 (0.0003) | serine: 0.16 | NCC(2.35) | |
| 0.03 (0.00018) | serine: 1.7 | NCC(2.41) | |
| 0.03 (0.00018) | serine: 0.5 | NCC(2.36) | |
| Comp. Ex. | | | |
| 0.33 (0.002) | serine: 0.83 | * (2.75) | oil drop |
| 0.11 (0.00066) | serine: 4.2 | * (2.61) | |
| 0.11 (0.00066) | serine: 0.13 | * (2.78) | |
| 0.02 (0.00012) | serine: 1.7 | * (3.12) | |
| 0.02 (0.00012) | serine: 0.16 | * (3.55) | |
| 0.54 (0.0032) | — | * (3.75) | oil drop |
| 0.44 (0.0026) | — | * (3.56) | oil drop |
| 0.22 (0.0013) | — | * (3.39) | |
| 0.11 (0.00066) | — | * (3.41) | |
| 0.06 (0.00036) | — | ** (4.19) | |
| — | serine: 3.4 | *** (6.45) | |
| — | serine: 1.0 | ** (5.92) | |
| — | serine: 0.32 | *** (6.29) | |
| — | — | *** (7.27) | oil drop |

[1] The amount of the stabilizer to be added is expressed in terms of part by weight per one part by weight of the emulsifying agent and each numerical value in the parenthesis indicates the amount of citric acid (part by weight) per one part by weight of the lipid emulsion, with the proviso that the amount of sodium citrate is expressed in terms of the amount of citric acid.
[2] This means the change in appearance observed after storing at 60° C. for three weeks.
[3] "NCC" means "no change of color". Each numerical value in the parenthesis indicates the corresponding value of ΔE.

EXAMPLE 3

After dissolving, in 20 ml of a hexane-ethanol (10:1) mixed solvent, 0.48 g of yolk lecithin [NC-10S (registered trademark), phosphatidylchorine(PC) purity of not less than 95%, available from Nippon Oil and Fats Co., Ltd.] and 0.12 g of yolk phosphatidyl-ethanolamine [NE-10 (registered trademark), phosphatidyletanolamine(PE) purity of not less than 95%, available from Nippon Oil and Fats Co., Ltd.], the solvent was distilled off under reduced pressure using an evaporator to form a lipid film. To the lipid film, there were added 5.4 g of soybean oil and 94 ml of a 2% glycerin aqueous solution and then the resulting mixture was preliminarily emulsified by vigorously stirring through shaking. Thereafter, the preliminarily emulsified liquid was passed through Microfluidizer (M-110 EH; available from Microfluidics Company) 10 times under a presure of 750 kg/cm$^2$ to thus emulsify the liquid. The pH value of the emulsified liquid was adjusted to the range of from 6.5 to 7.5 by the addition of NaOH to give a milk white stock lipid emulsion containing yolk lecithin.

Moreover, the same procedures used above were repeated except that 0.48 g of soybean lecithin [PCS (registered trade mark), PC purity of not less than 95%, available from Nippon Fine Chemical Co., Ltd.] was substituted for 0.48 g of the yolk lecithin used above to give a milk white stock lipid emulsion containing soybean lecithin.

In addition, the same procedures used above were repeated except that 0.42 g of yolk lecithin and 0.12 g of soybean lecithin were substituted for 0.48 g of the yolk lecithin used above and that the yolk phosphatidylethanolamine was used in an amount of 0.06 g instead of 0.12 g to give a milk white stock lipid emulsion containing yolk lecithin and soybean lecithin.

To one volume of each resulting stock lipid emulsion, there was added 0.2 volume of a 2% glycerin aqueous solution containing sodium citrate and histidine and whose pH was adjusted to a level identical to that of the stock lipid emulsion to give a lipid emulsion of the present invention. By way of comparison, to one volume of each stock lipid emulsion, there was added 0.2 volume of a 2% glycerin aqueous solution containing either sodium citrate or histidine and whose pH was adjusted to a level identical to that of the stock lipid emulsion or 0.2 volume of a simple 2% glycerin aqueous solution whose pH was adjusted to a level identical to that of the stock lipid emulsion to give each corresponding comparative lipid emulsion.

Each lipid emulsion prepared by the foregoing procedures was stored at 60° C. and then inspected for the change in appearance in the same manner used in Example 1. The change in appearance of each sample was observed after storing over one week. The results thus obtained are summarized in the following Table 3. The comparative lipid emulsions caused change of color, but all of the lipid emulsions of the present invention did not cause any change of color or formation of oil drops. This clearly indicate that all of the lipid emulsions comprising either or both of yolk lecithin and soybean lecithin are stable when they comprise the stabilizers of the present invention.

TABLE 3

| | Example 3 | | | |
|---|---|---|---|---|
| | Emulsi- | Stabilizer[1] | | Appearance[2] |
| | fying Agent | Citric Acid | Histidine | Change of Color[3] | Formation of Oil Drop |
| Present Invention | EPC | 0.013 | 0.1 | NCC (1.50) | |
| Comp. Ex. | EPC | 0.026 | — | * (2.91) | |
| Comp. Ex. | EPC | — | 0.2 | * (2.97) | |
| Comp. Ex. | EPC | — | — | ** (5.18) | |
| Present Invention | SPC | 0.013 | 0.1 | NCC (1.70) | |

TABLE 3-continued

| | Example 3 | | | |
|---|---|---|---|---|
| | Emulsi- | Stabilizer[1] | | Appearance[2] |
| | fying Agent | Citric Acid | Histidine | Change of Color[3] | Formation of Oil Drop |
| Comp. Ex. | SPC | 0.026 | — | * (2.87) | |
| Comp. Ex. | SPC | — | 0.2 | * (3.96) | |
| Comp. Ex. | SPC | — | — | ** (5.98) | |
| Present Invention | EPC + SPC | 0.013 | 0.1 | NCC (2.42) | |
| Comp. Ex. | EPC + SPC | 0.026 | — | * (3.04) | |
| Comp. Ex. | EPC + SPC | — | 0.2 | ** (5.12) | |
| Comp. Ex. | EPC + SPC | — | — | ** (4.93) | |

EPC: yolk lecithin; SPC: soybean lecithin
[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for one week.
[3]"NCC" means "no change of color". Each numerical value in the parenthesis indicates the corresponding value of ΔE.

EXAMPLE 4

After dissolving, in a chloroform or hexane-ethanol (10:1) mixed solvent, yolk lecithin and various phospholipids and auxiliary agents for emulsification listed in the following Table 4, the solvent was distilled off under reduced pressure using an evaporator to form lipid films having various compositions.

To the resulting lipid film, there were added 5.4 g of soybean oil and 94 ml of a 2% glycerin aqueous solution followed by vigorous stirring through shaking to carry out preliminary emulsification. Then each preliminarily emulsified liquid was passed through Microfluidizer 10 times under a presure of 750 kg/cm$^2$ to thus emulsify the liquid. The pH value of the emulsified liquid was adjusted to the range of from 6.5 to 7.5 by the addition of NaOH to give a milk white stock lipid emulsion containing yolk lecithin.

To one volume of the resulting stock lipid emulsion, there was added 0.2 volume of a 2% glycerin aqueous solution containing sodium citrate and histidine or serine and whose pH was adjusted to a level identical to that of the stock lipid emulsion to give a lipid emulsion of the present invention. By way of comparison, to one volume of the stock lipid emulsion, there was added 0.2 volume of a 2% glycerin aqueous solution containing one of sodium citrate, histidine and serine and whose pH was adjusted to a level identical to that of the stock lipid emulsion or 0.2 volume of a 2% glycerin aqueous solution whose pH was adjusted to a level identical to that of the stock lipid emulsion to give each corresponding comparative lipid emulsion.

Each lipid emulsion prepared by the foregoing procedures was stored at 60° C. and inspected, after one week, for the change in appearance in the same manner used in Example 1. The results thus obtained are summarized in the following Table 4. The comparative lipid emulsions caused change of color, but the lipid emulsions of the present invention did not cause change of color and did not cause any formation of oil drops. This clearly indicate that all of the lipid emulsions of the present invention prepared by mixing various kinds of phospholipids and/or auxiliary agents for emulsification are excellent in stability.

TABLE 4

Example 4

| Comp. of Emulsifying Agent[1] (wt %) | Stabilizer[2] Citric Acid | Stabilizer[2] Amino Acid | Appearance[3] Change of Color[4] | Appearance[3] Formation of Oil Drop |
|---|---|---|---|---|
| (Serine) | | | | |
| Present Inv. | PYL/DMPC | 0.039 | 0.6 | NCC(1.40) |
| Comp. Ex. (0.45/0.05) | 0.078 | — | * (3.14) | |
| | — | 1.2 | *** (10.32) | |
| | — | — | *** (10.59) | |
| (Serine) | | | | |
| Present Inv. | PYL/DPPC | 0.039 | 0.6 | NCC(1.42) |
| Comp. Ex. (0.45/0.05) | 0.078 | — | * (3.61) | |
| | — | 1.2 | *** (8.93) | |
| | — | — | *** (10.23) | |
| (Hisidine) | | | | |
| Present Inv. | EPC/EPE | 0.013 | 0.1 | NCC(2.49) |
| Comp. Ex. (0.35/0.15) | 0.026 | — | *** (7.18) | |
| | — | 0.2 | *** (8.11) | |
| | — | — | *** (13.97) | |
| ((Histidine) | | | | |
| Present Inv. | EPC/HEPC/EPE | 0.013 | 0.1 | NCC(1.62) |
| Comp. Ex. (0.4/0.05/0.05) | 0.026 | — | * (3.28) | |
| | — | 0.2 | * (3.76) | |
| (Serine) | | | | |
| Present Inv. | PYL/DPPA | 0.039 | 0.6 | NCC(2.31) |
| Comp. Ex. (0.45/0.05) | 0.078 | — | *** (8.51) | |
| | — | 1.2 | * (2.89) | |
| | — | — | ** (5.68) | |
| (Serine) | | | | |
| Present Inv. | PYL/chol. | 0.039 | 0.6 | NCC(2.28) |
| Comp. Ex. (0.45/0.05) | 0.078 | — | * (3.85) | |
| | — | 1.2 | *** (12.44) | |
| | — | — | *** (10.94) | |
| (Serine) | | | | |
| Present Inv. | EPC/EPE/oleic acid | 0.039 | 0.6 | NCC(1.37) |
| Comp. Ex. (0.425/0.05/0.025) | 0.078 | — | * (2.96) | |
| | — | 1.2 | ** (4.86) | |
| | — | — | ** (5.33) | |

[1]Composition of lipid emulsions and emulsifying agents:
Oil Component: 4.5% soybean oil
PYL (purified yolk lecithin): phosphatidylcholine (69.4%)/ lysophosphatidylcholine (1.9%)/phosphatidylethanolamine (19.7%)/other lipids (4.4%);
DMPC: dimyristoylphosphatidylcholine;
DPPC: dipalmitoylphosphatidylcholine;
EPC : yolk lecithin;
EPE : yolk phosphatidylethanolamine;
HEPC: hydrogenated yolk lecithin;
DPPA: dipalmitoylphosphatidic acid;
chol.: cholesterol
[2]The amount of the stabilizer added is expressed in terms of part by weight per one part by weight of the emulsifying agent, with the proviso that the amount of sodium citrate is expressed in terms of the amount of citric acid.
[3]This means the change in appearance observed after storing at 60° C. for one week.
[4]"NCC" means "no change of color". Each numerical value in the parenthesis indicates the corresponding value of ΔE.

EXAMPLE 5

After dissolving, in 20 ml of a hexane-ethanol (10:1) mixed solvent, 0.54 g of yolk lecithin and 0.06 g of yolk phosphatidylethanolamine, the solvent was distilled off under reduced pressure using an evaporator to form a lipid film. To the lipid film, there were added 5.4 g of soybean oil and 94 ml of a 2% glycerin aqueous solution followed by vigorous stirring through shaking to carry out preliminary emulsification. Then the preliminarily emulsified liquid was passed through Microfluidizer 10 times under a presure of 750 kg/cm$^2$ to thus emulsify the liquid. The pH value of the emulsified liquid was adjusted to the range of from 6.5 to 7.5 by the addition of NaOH to give a milk white stock lipid emulsion containing yolk lecithin.

To one volume of the resulting stock lipid emulsion, there was added 0.2 volume of a 2% glycerin aqueous solution containing sodium citrate and histidine and whose pH was adjusted to a level identical to that of the stock lipid emulsion to give a lipid emulsion of the present invention containing yolk lecithin in which the stabilizer was added after the emulsification step. By way of comparison, to one volume of the stock lipid emulsion, there was added 0.2 volume of a 2% glycerin aqueous solution whose pH was adjusted to a level identical to that of the stock lipid emulsion to give a comparative lipid emulsion.

After dissolving, in 20 ml of a hexane-ethanol (10:1) mixed solvent, 0.45 g of yolk lecithin and 0.05 g of yolk phosphatidylethanolamine, the solvent was distilled off under reduced pressure using an evaporator to form a lipid film. To the lipid film, there were added 4.5 g of soybean oil and 95 ml of a 2% glycerin aqueous solution which contained sodium citrate and histidine followed by vigorous stirring through shaking to carry out preliminary emulsification. Then the preliminarily emulsified liquid was passed through Microfluidizer 10 times under a presure of 750 kg/cm$^2$ to thus emulsify the liquid. The pH value of the emulsified liquid was adjusted to the range of from 6.5 to 7.5 by the addition of NaOH or HCl to give a lipid emulsion containing yolk lecithin in which the stabilizer was added prior to the emulsification step.

Each lipid emulsion prepared by the foregoing procedures was stored at 60° C. and inspected, after one week, for the change in appearance in the same manner used in Example 1. The results thus obtained are summarized in the following Table 5. It was found that the lipid emulsions to which the stabilizers were added before and after the emulsification step respectively had equal stability and were highly stable. Therefore, the foregoing results clearly prove that the effect of the present invention is independent of the method for adding stabilizers and that the lipid emulsion is always stable so far as it comprises the stabilizer of the present invention.

TABLE 5

Example 5

| | Stabilizer[1] Citric Acid | Stabilizer[1] Histidine | Appearance[2] Change of Color[3] | Appearance[2] Formation of Oil Drop |
|---|---|---|---|---|
| | Addition of stabilizer | | | |
| Present Inv. | Prior to Emulsification | 0.013 | 0.1 | NCC (1.95) |

TABLE 5-continued

| | | Example 5 | | | |
|---|---|---|---|---|---|
| | | Stabilizer[1] | | Appearance[2] | |
| | Addition of stabilizer | Citric Acid | Histi- dine | Change of Color[3] | Formation of Oil Drop |
| Present Inv. | After Emulsi- fication | 0.013 | 0.1 | NCC (2.01) | |
| Comp. Ex. | | — | — | ** (5.18) | |

[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for one week.
[3]"NCC" means "no change of color". Each numerical value in the parenthesis indicates the corresponding value of ΔE.

EXAMPLE 6

After dissolving, in 20 ml of a hexane-ethanol (10:1) mixed solvent, 0.54 g of yolk lecithin and 0.06 g of yolk phosphatidylethanolamine, the solvent was distilled off under reduced pressure using an evaporator to form a lipid film. To the lipid film, there were added 5.4 g of soybean oil and 94 ml of a 2% glycerin aqueous solution followed by vigorous stirring through shaking to carry out preliminary emulsification. Then the preliminarily emulsified liquid was passed through Microfluidizer 10 times under a presure of 750 kg/cm² to thus emulsify the liquid. The pH value of the emulsified liquid was adjusted to the range of from 6.5 to 7.5 by the addition of NaOH to give a milk white stock lipid emulsion containing yolk lecithin and soybean oil.

Moreover, the same procedures used above were repeated except that 5.4 g of Panacet 810 (registered trade mark, semi-synthetic medium chain triglyceride, available from Nippon Oil and Fats Co., Ltd.) was added instead of 5.4 g of soybean oil to give a milk white stock lipid emulsion containing yolk lecithin and Panacet 810.

After dissolving, in 20 ml of a hexane-ethanol (10:1) mixed solvent, 0.4 g of yolk lecithin and 0.2 g of Purified Yolk Lecithin (registered trade mark, PC 70%, PE 20%, available from Asahi Chemical Industry Co., Ltd.), the solvent was distilled off under reduced pressure using an evaporator to form a lipid film. To the lipid film, there were added 5.4 g of sesame oil and 94 ml of a 2% glycerin aqueous solution followed by vigorous stirring through shaking to carry out preliminary emulsification. Then the same procedures used above were repeated to give a milk white stock lipid emulsion containing yolk lecithin and sesame oil.

To one volume of each resulting stock lipid emulsion, there was added 0.2 volume of a 2% glycerin aqueous solution containing sodium citrate and serine or histidine and whose pH was adjusted to a level identical to that of the stock lipid emulsion to give a lipid emulsion of the present invention. By way of comparison, to one volume of each stock lipid emulsion, there was added 0.2 volume of a 2% glycerin aqueous solution containing one of sodium citrate, histidine and serine and whose pH was adjusted to a level identical to that of the stock lipid emulsion or 0.2 volume of a 2% glycerin aqueous solution whose pH was adjusted to a level identical to that of the stock lipid emulsion to give each corresponding comparative lipid emulsion.

Each lipid emulsion prepared by the foregoing procedures was stored at 60° C. and inspected, after one or two weeks, for the change in appearance in the same manner used in Example 1. The results thus obtained are summarized in the following Table 6. The results listed in Table 6 indicate that the lipid emulsions which comprise vegetable oils such as sesame oil and soybean oil, as the oil component, and/or synthetic or semi-synthetic glycerides such as Panacet® 810 can ensure the effect of the present invention.

TABLE 6-1

| | | Example 6 | | | |
|---|---|---|---|---|---|
| | Oil | Stabilizer[1] | | Appearance[2] | |
| | Component Used | Citric Acid | Amino Acid | Change of Color[3] | Formation of Oil Drop |
| (Serine) | | | | | |
| Present Inv. | Soybean Oil | 0.039 | 0.6 | NCC (1.67) | |
| Comp. Ex. | Soybean Oil | 0.078 | — | * (2.91) | |
| | | — | 1.2 | * (3.46) | |
| | | — | — | ** (5.18) | |
| (Serine) | | | | | |
| Present Inv. | Panacet 810 | 0.078 | 0.6 | NCC (2.37) | |
| Comp. Ex. | Panacet 810 | 0.156 | — | ** (4.25) | |
| | | — | 1.2 | *** (7.02) | |
| | | — | — | *** (13.50) | oil drop |
| (Histidine) | | | | | |
| Present Inv. | Sesame Oil | 0.013 | 0.1 | NCC (2.09) | |
| Comp. Ex. | Sesame Oil | 0.026 | — | * (2.77) | |
| | | — | 0.2 | *** (7.84) | |
| | | — | — | *** (10.11) | |

[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for one or two weeks.
[3]"NCC" means "no change of color". Each numerical value in the parenthesis indicates the corresponding value of ΔE.

EXAMPLE 7

After dissolving, in 20 ml of a hexane-ethanol (10:1) mixed solvent, 1.08 g of yolk lecithin and 0.12 g of yolk phosphatidylethanolamine, the solvent was distilled off under reduced pressure using an evaporator to form a lipid film. To the lipid film, there were added 0.6 g of soybean oil and 99 ml of a 2% glycerin aqueous solution followed by vigorous stirring through shaking to carry out preliminary emulsification. Then the preliminarily emulsified liquid was passed through Microfluidizer 10 times under a presure of 750 kg/cm2 to thus emulsify the liquid. The pH value of the emulsified liquid was adjusted to the range of from 6.5 to 7.5 by the addition of NaOH to give a milk white stock lipid emulsion containing yolk lecithin and 0.6% soybean oil.

Moreover there were dissolved, in 20 ml of a hexane-ethanol (10:1) mixed solvent, 0.047 g of yolk lecithin and 0.02 g of yolk phosphatidylethanolamine and then the solvent was distilled off under reduced pressure using an evaporator to form a lipid film. To the lipid film, there were added 0.6 g of soybean oil and 99.5 ml of a 2% glycerin aqueous solution followed by vigorous stirring through shaking to carry out preliminary emulsification. Then the same procedures used above were repeated to give a milk white stock lipid emulsion containing yolk lecithin and 0.6% soybean oil.

Furthermore, there were dissolved, in 20 ml of a hexane-ethanol (10:1) mixed solvent, 2.16 g of yolk lecithin and 0.24 g of yolk phosphatidylethanolamine and then the solvent was distilled off under reduced pressure using an evaporator to form a lipid film. To the lipid film, there were added 36 g of soybean oil and 60 ml of a 2% glycerin aqueous solution followed by vigorous stirring through shaking to carry out preliminary emulsification. Then the same procedures used above were repeated to give a milk white stock lipid emulsion containing yolk lecithin and 36% soybean oil.

To one volume of each resulting stock lipid emulsion, there was added 0.2 volume of a 2% glycerin aqueous solution containing sodium citrate and histidine and whose pH was adjusted to a level identical to that of the stock lipid emulsion to give a lipid emulsion of the present invention. By way of comparison, to one volume of each stock lipid emulsion, there was added 0.2 volume of a 2% glycerin aqueous solution containing either sodium citrate or histidine and whose pH was adjusted to a level identical to that of the stock lipid emulsion or 0.2 volume of a 2% glycerin aqueous solution whose pH was adjusted to a level identical to that of the stock lipid emulsion to give each corresponding comparative lipid emulsion.

Each lipid emulsion prepared by the foregoing procedures was stored at 60° C. and inspected, after one or two weeks, for the change in appearance in the same manner used in Example 1. The results thus obtained are summarized in the following Table 7. The results listed in Table 7 indicate that the lipid emulsions whose content of the oil component ranges from 0.5 to 30% can ensure the effect of the present invention.

TABLE 7

Example 7

| Oil Content (Emulsifying Agent Content) | Time of Storage (week) | Stabilizer[1] Citric Acid | Stabilizer[1] Histidine | Appearance[2] Change of Color[3] | Appearance[2] Formation of Oil Drop |
|---|---|---|---|---|---|
| Present Inv. 0.5% (1%) | 1 | 0.065 | 0.05 | NCC (2.25) | |
| Comp. Ex. 0.5% (1%) | 1 | 0.130 | — | *** (8.06) | |
| | | — | 0.1 | *** (8.00) | |
| | | — | — | *** (9.25) | |
| Present Inv. 0.5% (0.056%) | 2 | 0.058 | 0.36 | NCC (2.04) | |
| Comp. Ex. 0.5% (0.056%) | 2 | 0.116 | — | * (2.54) | |
| | | — | 0.72 | *** (8.43) | |
| | | — | — | *** (10.11) | oil drop |
| Present Inv. 30% (2%) | 1 | 0.04 | 0.025 | NCC (2.30) | |
| Comp. Ex. 30% (2%) | 1 | 0.08 | — | ** (5.40) | |
| | | — | 0.05 | ** (2.71) | |
| | | — | — | * (3.53) | oil drop |

[1] The amount of the stabilizer added is expressed in terms of part by weight per one part by weight of the emulsifying agent, with the proviso that the amount of sodium citrate is expressed in terms of the amount of citric acid.
[2] This means the change in appearance observed after storing at 60° C. for one or two weeks.
[3] "NCC" means "no change of color". Each numerical value in the parenthesis indicates the corresponding value of ΔE.

EXAMPLE 8

After dissolving, in 20 ml of a hexane-ethanol (10:1) mixed solvent, 2.16 g of yolk lecithin and 0.24 g of yolk phosphatidylethanolamine, the solvent was distilled off under reduced pressure using an evaporator to form a lipid film. To the lipid film, there were added 1.2 g of soybean oil and 98 ml of a 2% glycerin aqueous solution followed by vigorous stirring through shaking to carry out preliminary emulsification. Then the preliminarily emulsified liquid was passed through Microfluidizer 10 times under a presure of 750 kg/cm² to thus emulsify the liquid. The pH value of the emulsified liquid was adjusted to the range of from 6.5 to 7.5 by the addition of NaOH to give a milk white stock lipid emulsion having a weight ratio: emulsifying agent/oil component of 2.

Moreover there were dissolved, in 20 ml of a hexane-ethanol (10:1) mixed solvent, 0.36 g of yolk lecithin and 0.04 g of yolk phosphatidylethanolamine and then the solvent was distilled off under reduced pressure using an evaporator to form a lipid film. To the lipid film, there were added 12 g of soybean oil and 87 ml of a 2% glycerin aqueous solution followed by vigorous stirring through shaking to carry out preliminary emulsification. Then the same procedures used above were repeated to give a milk white stock lipid emulsion having a weight ratio: emulsifying agent/oil component of 1/30.

To one volume of each resulting stock lipid emulsion, there was added 0.2 volume of a 2% glycerin aqueous solution containing sodium citrate and histidine and whose pH was adjusted to a level identical to that of the stock lipid emulsion to give a lipid emulsion of the present invention. By way of comparison, to one volume of each stock lipid emulsion, there was added 0.2 volume of a 2% glycerin aqueous solution containing either sodium citrate or histidine and whose pH was adjusted to a level identical to that of the stock lipid emulsion or 0.2 volume of a 2% glycerin aqueous solution whose pH was adjusted to a level identical to that of the stock lipid emulsion to give a comparative lipid emulsion.

Each lipid emulsion prepared by the foregoing procedures was stored at 60° C. and inspected, after one week, for the change in appearance in the same manner used in Example 1. The results thus obtained are summarized in the following Table 8. The results listed in Table 8 indicate that the lipid emulsions whose weight ratio: emulsifying agent/oil component ranges from 1/30 to 2 can ensure the intended effect of the present invention.

TABLE 8

Example 8

| Emulsifying Agent/Oil Component (wt. ratio) | Stabilizer[1] Citric Acid | Stabilizer[1] Histidine | Appearance[2] Change of Color[3] | Appearance[2] Formation of Oil Drop |
|---|---|---|---|---|
| Present Inv. 2 | 0.065 | 0.05 | NCC (2.45) | |
| Comp. Ex. 2 | 0.130 | — | *** (10.28) | |
| | — | 0.1 | *** (6.42) | |
| | — | — | *** (12.85) | |
| Present Inv. 1/30 | 0.1 | 0.15 | NCC (2.47) | |
| Comp. Ex. 1/30 | 0.2 | — | *** (9.23) | |
| | — | 0.30 | * (3.03) | |
| | — | — | ** (4.48) | |

[1] The amount of the stabilizer added is expressed in terms of part by weight per one part by weight of the emulsifying agent with the proviso that the amount of sodium citrate is expressed in terms of the amount of citric acid.
[2] This means the change in appearance observed after storing at 60° C. for one week.
[3] "NCC" means "no change of color". Each numerical value in the parenthesis indicates the corresponding value of ΔE.

EXAMPLE 9

To one volume of a commercially available lipid emulsion containing dexamethasone palmitate (Limethason®), there was added one volume of a 2% glycerin aqueous solution containing sodium citrate and histidine and whose pH was adjusted to 7.0 to give a lipid emulsion of the present invention. By way of comparison, one volume of a 2% glycerin aqueous solution containing sodium citrate or histidine and whose pH was adjusted to 7.0 or a 2% glycerin aqueous solution whose pH was adjusted to 7.0 was added to one volume of Limethason to give each corresponding comparative lipid emulsion.

Each lipid emulsion prepared by the foregoing procedures was stored at 60° C. and inspected, after two weeks, for the change in appearance in the same manner used in Example 1. The results thus obtained are summarized in the following Table 9. As a result, it was found that the comparative lipid emulsions caused change of color, while the lipid emulsion of the present invention did not cause any change of color or formation of oil drops. This clearly indicates that the lipid emulsion of the invention is quite stable. Therefore, it is clear that the present invention can also be applied to dexamethasone palmitate-containing lipid emulsion.

EXAMPLE 10

To one volume of a commercially available lipid emulsion containing flurbiprofen axetil (Lipfen®), there was added one volume of a 2% glycerin aqueous solution containing sodium citrate and histidine and whose pH was adjusted to 7.0 to give a lipid emulsion of the present invention. By way of comparison, one volume of a 2% glycerin aqueous solution containing sodium citrate or histidine and whose pH was adjusted to 7.0 or a 2% glycerin aqueous solution whose pH was adjusted to 7.0 was added to one volume of Lipfen to give each corresponding comparative lipid emulsion.

Each lipid emulsion prepared by the foregoing procedures was stored at 60° C. and inspected, after two weeks, for the change in appearance in the same manner used in Example 1. The results thus obtained are summarized in the following Table 9. As a result, it was found that the comparative lipid emulsions caused change of color, while the lipid emulsion of the present invention did not cause any change of color or formation of oil drops. This clearly indicates that the lipid emulsion of the invention is quite stable. Therefore, it is clear that the present invention can also be applied to flurbiprofen axetil-containing lipid emulsion.

TABLE 9

| | | | Examples 9 and 10 | | |
| | | Time | Stabilizer[1] | Appearance[2] | |
| | Drug Used (wt %) | of Storage (week) | Citric Acid | Histi- dine | Change of Color[3] | Formation of Oil Drop |
|---|---|---|---|---|---|---|
| Example 9 | | | | | | |
| Present Inv. | Dexame- thasone | 2 | 0.011 | 0.083 | NCC (2.26) | |
| Comp. Ex. | Palmitate | 2 | 0.022 | — | * (3.38) | |
| | | | — | 0.166 | *** (6.03) | |
| | | | — | — | *** (7.42) | |
| Example 10 | | | | | | |
| Present Inv. | Flurbi- profen | 2 | 0.011 | 0.083 | NCC (1.74) | |

TABLE 9-continued

| | | Examples 9 and 10 | | |
| | | Time | Stabilizer[1] | Appearance[2] |
| | Drug Used (wt %) | of Storage (week) | Citric Acid | Histi- dine | Change of Color[3] | Formation of Oil Drop |
|---|---|---|---|---|---|---|
| Comp. Ex. | Axetil | 2 | 0.022 | — | * (2.84) | |
| | | | — | 0.166 | * (3.11) | |
| | | | — | — | ** (5.34) | |

[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for two weeks.
[3]"NCC" means "no change of color". Each numerical value in the parenthesis indicates the corresponding value of ΔE.

EXAMPLE 11

There were dissolved, in 20 ml of a hexane-ethanol (10:1) mixed solvent, 0.54 g of yolk lecithin and 0.06 g of yolk phosphatidylethanolamine. Separately, 0.012 g of fluorometholone was dissolved in 20 ml of ethanol, the resulting solution was added to the foregoing phospholipid solution followed by sufficient mixing. Thereafter, the solvent was distilled off under reduced pressure using an evaporator to form a drug-containing lipid film. To the lipid film, there were added 5.4 g of soybean oil and 94 ml of a 2% glycerin aqueous solution followed by vigorous stirring through shaking to carry out preliminary emulsification. Then the preliminarily emulsified liquid was passed through Microfluidizer 10 times under a presure of 750 kg/cm$^2$ to thus emulsify the liquid. The pH value of the emulsified liquid was adjusted to the range of from 6.5 to 7.5 by the addition of NaOH or HCl to give a milk white stock lipid emulsion containing yolk lecithin and fluorometholone.

EXAMPLE 12

The same procedures used in. Example 11 were repeated except that 0.06 g of fluorouracil was substituted for 0.012 g of fluorometholone to give a milk white stock lipid emulsion containing yolk lecithin and fluorouracil.

EXAMPLE 13

The same procedures used in Example 11 were repeated except that 0.06 g of tranilast was substituted for 0.012 g of fluorometholone to give a milk white stock lipid emulsion containing yolk lecithin and tranilast.

EXAMPLE 14

The same procedures used in Example 11 were repeated except that 0.06 g of ofloxacin was substituted for 0.012 g of fluorometholone to give a milk white stock lipid emulsion containing yolk lecithin and ofloxacin,

EXAMPLE 15

The same procedures used in Example 11 were repeated except that 0.06 g of ciclosporin was substituted for 0.012 g of fluorometholone to give a milk white stock lipid emulsion containing yolk lecithin and ciclosporin.

EXAMPLE 16

The same procedures used in Example 11 were repeated except that 0.06 g of diclofenac was substituted for 0.012 g of fluorometholone to give a milk white stock lipid emulsion containing yolk lecithin and diclofenac.

EXAMPLE 17

The same procedures used in Example 11 were repeated except that 0.00006 g of prostaglandin $E_1$ was substituted for 0.012 g of fluorometholone to give a milk white stock lipid emulsion containing yolk lecithin and prostaglandin $E_1$.

EXAMPLE 18

The same procedures used in Example 11 were repeated except that 0.012 g of betamethasone was substituted for 0.012 g of fluorometholone to give a milk white stock lipid emulsion containing yolk lecithin and betamethasone.

EXAMPLE 19

The same procedures used in Example 11 were repeated except that 0.012 g of prednisolone was substituted for 0.012 g of fluorometholone to give a milk white stock lipid emulsion containing yolk lecithin and prednisolone.

EXAMPLE 20

The same procedures used in Example 11 were repeated except that 0.012 g of amphotericin B was substituted for 0.012 g of fluorometholone to give a faint yellow stock lipid emulsion containing yolk lecithin and amphotericin B.

EXAMPLE 21

The same procedures used in Example 11 were repeated except that 0.06 g of erythromycin was substituted for 0.012 g of fluorometholone to give a milk white stock lipid emulsion containing yolk lecithin and erythromycin.

EXAMPLE 22

The same procedures used in Example 11 were repeated except that 0.12 g of theophylline was substituted for 0.012 g of fluorometholone to give a milk white stock lipid emulsion containing yolk lecithin and theophylline.

To one volume of each stock lipid emulsion prepared in Examples 11 to 22, there was added 0.2 volume of a 2% glycerin aqueous solution containing sodium citrate and serine or histidine and whose pH was adjusted to a level identical to that of the stock lipid emulsion to give a drug-containing lipid emulsion of the present invention. By way of comparison, to one volume of each stock lipid emulsion, there was added 0.2 volume of a 2% glycerin aqueous solution containing one of sodium citrate, serine and histidine and whose pH was adjusted to a level identical to that of the stock lipid emulsion or 0.2 volume of a 2% glycerin aqueous solution whose pH was adjusted to a level identical to that of the stock lipid emulsion to give each corresponding drug-containing comparative lipid emulsion.

Each lipid emulsion prepared by the foregoing procedures was stored at 60° C. and inspected, after one week and 12 days, for the change in appearance in the same manner used in Example 1. The results thus obtained are summarized in the following Table 10. As a result, it was found that the comparative lipid emulsions caused change of color and formation of oil drops, while the lipid emulsion of the present invention did not cause any change of color or formation of oil drops. This clearly indicates that the lipid emulsions of the present invention comprising various kinds of drugs are quite stable.

TABLE 10

Examples 11 to 22

| | Drug Used (wt %) | Storage Time (week) | Stabilizer[1] Citric Acid | Histidine | Appearance[2] Change of Color[3] | Formation of Oil Drop |
|---|---|---|---|---|---|---|
| Ex. 11: Serine | | | | | | |
| Present Inv. | fluorometholone | 1 | 0.04 | 0.6 | NCC | (2.15) |
| Comp. Ex. | | 1 | 0.08 | — | * | (3.02) |
| | | | — | 1.2 | ** | (4.23) |
| | | | — | — | ** | (4.66) |
| Ex. 12: Histidine | | | | | | |
| Present Inv. | fluorouracil | 1 | 0.065 | 0.1 | NCC | (1.74) |
| Comp. Ex. | | 1 | 0.130 | — | ** | (4.01) |
| | | | — | 0.2 | ** | (4.17) |
| | | | — | — | ** | (5.17) |
| Ex. 13: Serine | | | | | | |
| Present Inv. | tranilast | 1 | 0.11 | 0.6 | NCC | (1.50) |
| Comp. Ex. | | 1 | 0.22 | — | * | (3.26) |
| | | | — | 1.2 | *** | (6.19) |
| | | | — | — | *** | (6.70) |
| Ex. 14: Histidine | | | | | | |
| Present Inv. | ofloxacin | 1 | 0.065 | 0.1 | NCC | (2.48) |
| Comp. Ex. | | 1 | 0.130 | — | * | (3.08) |
| | | | — | 0.2 | * | (3.23) |
| | | | — | — | * | (3.76) |
| Ex. 15: Histidine | | | | | | |
| Present Inv. | ciclosporin | 1 | 0.065 | 0.1 | NCC | (1.41) |
| Comp. Ex. | | 1 | 0.130 | — | * | (3.01) |
| | | | — | 0.2 | * | (2.64) |
| | | | — | — | ** | (4.99) |
| Ex. 16: Histidine | | | | | | |
| Present Inv. | diclofenac | 1 | 0.065 | 0.1 | NCC | (2.07) |
| Comp. Ex. | | 1 | 0.130 | — | * | (3.89) |
| | | | — | 0.2 | ** | (5.14) |
| | | | — | — | *** | (6.74) |
| Ex. 17: Histidine | | | | | | |
| Present Inv. | prostaglandin $E_1$ | 1 | 0.065 | 0.1 | NCC | (1.29) |
| Comp. Ex. | | 1 | 0.130 | — | * | (3.76) |
| | | | — | 0.2 | * | (2.96) |
| | | | — | — | ** | (4.93) |
| Ex. 18: Serine | | | | | | |
| Present Inv. | betamethasone | 1 | 0.11 | 0.6 | NCC | (2.30) |
| Comp. Ex. | | 1 | 0.22 | — | * | (3.04) |
| | | | — | 1.2 | *** | (6.20) |
| | | | — | — | *** | (6.25) |
| Ex. 19: Histidine | | | | | | |
| Present Inv. | prednisolone | 1 | 0.065 | 0.1 | NCC | (1.99) |
| Comp. Ex. | | 1 | 0.130 | — | * | (3.20) |

TABLE 10-continued

Examples 11 to 22

| Drug Used (wt %) | | Storage Time (week) | Stabilizer[1] Citric Acid | Histidine | Appearance[2] Change of Color[3] | Formation of Oil Drop |
|---|---|---|---|---|---|---|
| | | | — | 0.2 | ** (5.48) | |
| | | | — | — | ** (5.14) | |
| Ex. 20: Histidine | | | | | | |
| Present Inv. | amphotericin B | 12 days | 0.065 | 0.1 | NCC (1.25) | |
| Comp. Ex. | | 12 days | 0.130 | — | * (2.63) | |
| | | | — | 0.2 | * (3.40) | |
| | | | — | — | ** (5.22) | oil drop |
| Ex. 21: Histidine | | | | | | |
| Present Inv. | erythromycin | 1 | 0.013 | 0.1 | NCC (2.47) | |
| Comp. Ex. | | 1 | 0.026 | — | ** (4.28) | |
| | | | — | 0.2 | ** (5.00) | |
| | | | — | — | *** (10.85) | |
| Ex. 22: Histidine | | | | | | |
| Present Inv. | theophylline | 1 | 0.065 | 0.1 | NCC (2.47) | |
| Comp. Ex. | | 1 | 0.130 | — | ** (5.03) | |
| | | | — | 0.2 | * (3.21) | |
| | | | — | — | *** (6.43) | |

[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for one week or 12 days.
[3]"NCC" means "no change of color". Each numerical value in the parenthesis indicates the corresponding value of ΔE.

EXAMPLE 23

After dissolving, in 20 ml of a hexane-ethanol (10:1) mixed solvent, 0.42 g of yolk lecithin and 0.18 g of purified yolk lecithin, the solvent was distilled off under reduced pressure using an evaporator to form a lipid film. Separately, 0.06 g of tocopherol acetate was added to 5.4 g of soybean oil and the resulting mixture was sufficiently stirred. To the lipid film, there were added the resulting mixture and 94 ml of a 2% glycerin aqueous solution followed by vigorous stirring through shaking to carry out preliminary emulsification. Then the preliminarily emulsified liquid was passed through Microfluidizer 10 times under a presure of 750 kg/cm² to thus emulsify the liquid. The pH value of the emulsified liquid was adjusted to the range of from 6.8 to 7.2 by the addition of NaOH to give a milk white stock lipid emulsion containing yolk lecithin and tocopherol acetate.

To one volume of the resulting tocopherol acetate-containing stock lipid emulsion thus prepared, there was added 0.2 volume of a 2% glycerin aqueous solution containing sodium citrate and histidine and whose pH was adjusted to a level identical to that of the stock lipid emulsion to give a lipid emulsion of the present invention. By way of comparison, to one volume of the foregoing stock lipid emulsion, there was added 0.2 volume of a 2% glycerin aqueous solution containing either sodium citrate or histidine and whose pH was adjusted to a level identical to that of the stock lipid emulsion or 0.2 volume of a 2% glycerin aqueous solution whose pH was adjusted to a level identical to that of the stock lipid emulsion to give each corresponding comparative lipid emulsion containing tocopherol acetate.

Each lipid emulsion prepared by the foregoing procedures was stored at 60° C. and inspected, after one week, for the change in appearance in the same manner used in Example 1. The results thus obtained are summarized in the following Table 11. As a result, it was found that the comparative lipid emulsions caused change of color, while the lipid emulsion of the present invention did not cause any change of color or formation of oil drops. This clearly indicates that the lipid emulsion of the invention is quite stable.

TABLE 11

Example 23

| Drug Used (wt %) | | Storage Time (week) | Stabilizer[1] Citric Acid | Histidine | Appearance[2] Change of Color[3] | Formation of Oil Drop |
|---|---|---|---|---|---|---|
| Present Inv. | tocopherol acetate | 1 | 0.065 | 0.1 | NCC (2.16) | |
| Comp. Ex. | | 1 | 0.130 | — | *(3.88) | |
| | | | — | 0.2 | **(5.85) | |
| | | | — | — | ***(15.22) | oil drop |

[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for one week.
[3]"NCC" means "no change of color". Each numerical value in the parenthesis indicates the corresponding value of ΔE.

EXAMPLE 24

After dissolving, in 20 ml of a hexane-ethanol (10:1) mixed solvent, 0.54 g of yolk lecithin and 0.06 g of yolk phosphatidylethanolamine. Separately, 0.12 g of tropicamide was dissolved in 20 ml of ethanol and the resulting solution was added to the foregoing lipid solution followed by sufficient stirring. The solvent was then distilled off under reduced pressure using an evaporator to form a drug-containing lipid film. To the lipid film, there were added 5.4 g of soybean oil and 94 ml of a 2% glycerin aqueous solution followed by vigorous stirring through shaking to carry out preliminary emulsification. Then the preliminarily emulsified liquid was passed through Microfluidizer® 10 times under a presure of 750 kg/cm² to thus emulsify the liquid. The pH value of the emulsified liquid was adjusted to the range of from 7.8 to 8.2 by the addition of NaOH or HCl to give a milk white stock lipid emulsion containing yolk lecithin and tropicamide.

EXAMPLE 25

The same procedures used in Example 24 were repeated except that 0.06 g of diphenhydramine was substituted for 0.12 g of tropicamide to give a milk white stock lipid emulsion containing yolk lecithin and diphenhydramine.

EXAMPLE 26

The same procedures used in Example 24 were repeated except that 0.03 g of naphazoline was substituted for 0.12 g of tropicamide to give a milk white stock lipid emulsion containing yolk lecithin and naphazoline.

To one volume of each stock lipid emulsion prepared in Example 24 to 26, there was added 0.2 volume of a 2% glycerin aqueous solution containing sodium citrate and histidine and whose pH was adjusted to a level identical to that of the stock lipid emulsion to give a lipid emulsion of the present invention. By way of comparison, to one volume of each stock lipid emulsion, there was added 0.2 volume of a 2% glycerin aqueous solution containing either sodium citrate or histidine and whose pH was adjusted to a level identical to that of the stock lipid emulsion or 0.2 volume of a 2% glycerin aqueous solution whose pH was adjusted to a level identical to that of the stock lipid emulsion to give each corresponding drug-containing comparative lipid emulsion.

Each lipid emulsion prepared by the foregoing procedures was stored at 60° C. and inspected, after one or two weeks, for the change in appearance in the same manner used in Example 1. The results thus obtained are summarized in the following Table 12. As a result, it was found that the comparative lipid emulsions caused change of color and formation of oil drops, while the lipid emulsion of the present invention did not cause any change of color or formation of oil drops. This clearly indicates that the lipid emulsions of the invention comprising various kinds of drugs are quite stable.

TABLE 12

| | | | | Examples 24 to 26 | |
|---|---|---|---|---|---|
| | | Sto- | | Appearance[2] | |
| | Drug | rage | Stabilizer[1] | Change | Formation |
| | Used (wt %) | Time (week) | Citric Acid | Histi- dine | of Color[3] | of Oil Drop |

Ex. 24

| Present Inv. | tropica- mide | 1 1 | 0.065 0.130 | 0.1 — | NCC (1.75) **(4.78) | |
| Comp. Ex. | | | — — | 0.2 — | **(4.43) **(5.57) | |

Ex. 25

| Present Inv. | diphen- hyd- | 2 2 | 0.013 0.26 | 0.1 — | NCC (2.19) **(5.47) | |
| Comp. Ex. | ramine | | — — | 0.2 — | **(5.30) ***(7.69) | oil drop |

Ex. 26

| Present Inv. | naphazo- line | 1 1 | 0.065 0.130 | 0.1 — | NCC (1.21) **(4.36) | |
| Comp. Ex. | | | — — | 0.2 — | *(2.93) **(4.90) | |

[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for one week.
[3]"NCC" means "no change of color". Each numerical value in the parenthesis indicates the corresponding value of ΔE.

EXAMPLE 27

To one volume of a 2% glycerin aqueous solution containing 0.24% lidocaine hydrochloride, there was added one volume of a commercially available lipid emulsion (Intralipos (registered trade mark) 10%). Then the pH value thereof was adjusted to 9.0 by addition of NaOH, followed by sufficient mixing at room temperature to give a milk white stock lipid emulsion containing yolk lecithin and lidocaine hydrochloride.

To one volume of the resulting stock lipid emulsion, there was added 0.2 volume of a 2% glycerin aqueous solution containing sodium citrate and histidine and whose pH was adjusted to 9.0 to give a drug-containing lipid emulsion of the present invention. By way of comparison, to one volume of the foregoing stock lipid emulsion, there was added 0.2 volume of a 2% glycerin aqueous solution containing either sodium citrate or histidine and whose pH was adjusted to 9.0 or a 2% glycerin aqueous solution whose pH was adjusted to 9.0 to give each corresponding comparative lipid emulsion.

Each lipid emulsion prepared by the foregoing procedures was stored at 60° C. and inspected, after two weeks, for the change in appearance in the same manner used in Example 1. The results thus obtained are summarized in the following Table 13. As a result, it was found that the comparative lipid emulsions caused change of color, while the lipid emulsion of the present invention did not cause any change of color or formation of oil drops. This clearly indicates that the lipid emulsion of the invention is quite stable.

TABLE 13

| | | | Example 27 | | |
|---|---|---|---|---|---|
| | | Sto- | | Appearance[2] | |
| | Drug | rage | Stabilizer[1] | Change | Formation |
| | Used (wt %) | Time (week) | Citric Acid | Histi- dine | of Color[3] | of Oil Drop |
| Present Inv. Comp. Ex. | lidocaine. HCl | 2 2 | 0.054 0.108 — — | 0.083 — 0.166 — | NCC (2.17) *(2.84) **(5.82) ***(6.32) | |

[1]The amount of the stabilizer added is expressed in terms of part by weight per one part by weight of the emulsifying agent, with the proviso that the amount of sodium citrate is expressed in terms of the amount of citric acid.
[2]This means the change in appearance observed after storing at 60° C. for one week.
[3]"NCC" means "no change of color". Each numerical value in the parenthesis indicates the corresponding value of ΔE.

EXAMPLE 28

Injection

The lipid emulsion (0.5 ml) obtained in Example 9 containing 0.01% sodium citrate, 0.05% histidine and 0.2% dexamethasone palmitate was charged in a 1 ml volume glass ampoule and sterilized by heating them at 60° C. for one hour. The sterilization was repeated three times every 24 hours to give an injection.

EXAMPLE 29

Injection

The lipid emulsion (2.5 ml) obtained in Example 10 containing 0.01% sodium citrate, 0.05% histidine and 0.5% flurbiprofen axetil was charged in 5 ml volume glass ampoule and sterilized by heating them at 60° C. for one hour. The sterilization was repeated three times every 24 hours to give an injection.

EXAMPLE 30

Nasal Drop

To the lipid emulsion obtained in Example 19 containing 0.05% sodium citrate, 0.05% histidine and 0.01% prednisolone, there were added methyl p-hydroxybenzoate and propyl p-hydroxybenzoate in such amounts that the final concentrations thereof in the lipid emulsion were 0.026% and 0.014%, respectively. The lipid emulsion was sterilized by filtration and then charged in a container for spraying to give a nasal drop.

EXAMPLE 31

Liniment

To the lipid emulsion obtained in Example 16 containing 0.05% sodium citrate, 0.05% histidine and 0.05% diclofenac, there were added methyl p-hydroxybenzoate and propyl p-hydroxybenzoate in such amounts that the final concentrations thereof in the lipid emulsion were 0.026% and 0.014%, respectively. The lipid emulsion was sterilized by filtration and then charged in a plastic container with sponge to give a liniment.

EXAMPLE 32

Inhalant

To the lipid emulsion obtained in Example 19 containing 0.05% sodium citrate, 0.05% histidine and 0.01% prednisolone, there were added methyl p-hydroxybenzoate and propyl p-hydroxybenzoate in such amounts that the final concentrations thereof in the lipid emulsion were 0.026% and 0.014%, respectively. The lipid emulsion was sterilized by filtration and then charged in a container for nebulizer to give an inhalant.

EXAMPLE 33

Drug for Oral Administration

The lipid emulsion obtained in Example 14 containing 0.05% sodium citrate, 0.05% histidine and 0.05% ofloxacin was filtered through a 0.45μm membrane filter and then charged in a glass container to give an oral drug.

EXAMPLE 34

Eye Drop

To the lipid emulsion obtained in Example 11 containing 0.03% sodium citrate, 0.3% serine and 0.01% fluorometholone, there were added methyl p-hydroxybenzoate and propyl p-hydroxybenzoate in such amounts that the final concentrations thereof in the lipid emulsion were 0.026% and 0.014%, respectively. The lipid emulsion was sterilized by filtration and then charged in a 5 ml volume eye drop bottle to give an eye drop.

EXAMPLE 35

Eye Drop

To the lipid emulsion obtained in Example 16 containing 0.05% sodium citrate, 0.05% histidine and 0.05% diclofenac, there were added methyl p-hydroxybenzoate and propyl p-hydroxybenzoate in such amounts that the final concentrations thereof in the lipid emulsion were 0.026% and 0.014%, respectively. The lipid emulsion was sterilized by filtration and then charged in a 5 ml volume eye drop bottle to give an eye drop.

EXAMPLE 36

Eye Drop

To the lipid emulsion obtained in Example 14 containing 0.05% sodium citrate, 0.05% serine and 0.05% ofloxacin, there were added methyl p-hydroxybenzoate and propyl p-hydroxybenzoate in such amounts that the final concentrations thereof in the lipid emulsion were 0.026% and 0.014%, respectively. The lipid emulsion was sterilized by filtration and then charged in a 5 ml volume eye drop bottle to give an eye drop.

As has been discussed above in detail, the present invention can provide a lipid emulsion excellent in storage stability and free of change of color and formation of oil drops through the use of cheap and highly safe natural phospholipids.

What is claimed is:

1. A lipid emulsion which comprises a drug and
    (A) an oil component,
    (B) from 1/50 to 3 part by weight of the oil component (A) of an emulsifying agent containing yolk lecithin and/or soybean lecithin, and
    (C) water wherein said lipid emulsion comprises citric acid or a pharmaceutically acceptable salt thereof and at least one member selected from the group consisting of methionine, phenylalanine, serine, histidine and pharmaceutically acceptable salts thereof, provided that said lipid emulsion does not simultaneously contain methionine and phenylalanine, wherein citric acid or its pharmaceutically acceptable salt is present in an amount of 0.01 to 0.27 part weight per one part by weight of the emulsifying and not more than 0.0016 part by weight per one part by weight of the lipid emulsion, with proviso that the amount of the salt of citric acid is expressed in terms of the amount of citric acid said histidine or its pharmaceutically acceptable salt is present in an amount of 0.008 to 0.83 part by weight per one part by weight of the emulsifying agent, with the proviso that the amount of the salt of histidine is expressed in terms of the amount of histidine, said methionine or its pharmaceutically acceptable salt is present in an amount of 0.08 to 1.7 part by weight per one part by weight of the emulsifying agent, with the proviso that the amount of the salt of methionine is expressed in terms of the amount of methionine, said phenylalanine or its pharmaceutically acceptable salt is resent in an amount of 0.4 to 0.83 part weight per one part weight of the emulsifying agent, with the proviso that the amount of the salt of phenylalanine is expressed in terms of the amount of phenylalanine, and said serine or its pharmaceutically acceptable salt is present in an amount of 0.16 to 2.9 parts by weight per one part by weight of the emulsifying agent with the proviso that the amount of the salt of serine is expressed terms of the amount of serine.

2. The lipid emulsion of claim 1 wherein it comprises:
    citric acid or its pharmaceutically acceptable salt in an amount of 0.01 to 0.27 part by weight per one part by weight of the emulsifying agent and not more than 0.0016 part by weight per one part by weight of the lipid emulsion, with the proviso that the amount of the salt of citric acid is expressed in terms of the amount the amount of citric acid, and histidine or its pharmaceutically acceptable salt in an amount of 0.008 to 0.83 part by weight per one part by weight of the emulsifying agent, with the proviso that the amount of the salt of histidine is expressed in terms of the amount of histidine.

3. The lipid emulsion of claim 1 wherein it comprises:
    citric acid or its pharmaceutically acceptable salt in an amount of 0.027 to 0.27 part by weight per one part by weight of the emulsifying agent and not more than 0.0016 part by weight per one part by weight of the lipid emulsion, with the proviso that the amount of the salt of citric acid is expressed in terms of the amount of citric acid, and methionine or its pharmaceutically acceptable salt in an amount of 0.08 to 1.7 parts by weight per one part by weight of the emulsifying agent, with the proviso that the amount of the salt of methionine is expressed in terms of the amount of methionine.

4. The lipid emulsion of claim 1 wherein it comprises:

citric acid or its pharmaceutically acceptable salt in an amount of 0.05 to 0.22 part by weight per one part by weight of the emulsifying agent and not more than 0.0016 part by weight per one part by weight of the lipid emulsion, with the proviso that the amount of the salt of citric acid is expressed in terms of the amount of citric acid, and phenylalanine or its pharmaceutically acceptable salt in an amount of 0.4 to 0.83 part by weight per one part by weight of the emulsifying agent, with the proviso that the amount of the salt of phenylalanine is expressed in terms of the amount of phenylalanine.

5. The lipid emulsion of claim 1 wherein it comprises:

citric acid or its pharmaceutically acceptable salt in an amount of 0.03 to 0.27 part by weight per one part by weight of the emulsifying agent and not more than 0.0016 part by weight per one part by weight of the lipid emulsion, with the proviso that the amount of the salt of citric acid is expressed in terms of the amount of citric acid, and serine or its pharmaceutically acceptable salt in an amount of 0.16 to 2.9 parts by weight per one part by weight of the emulsifying agent, with the proviso that the amount of the salt of serine is expressed in terms of the amount of serine.

6. The lipid emulsion according to claim 1 wherein the drug is a member selected from the group consisting of hypnotics, sedatives, antianxiety agents, antiepiletics, antipyretics, analgesics, antiinflammatories, antidepressants, tranquilizers, local anesthetics, sympatholytics, antispasmodics, antiglaucoma drugs, anticataract drugs, mydriatics, miotics, cardiotonics, antiarrhythmic agents, diuretics, antihypertensives, vasoconstrictors, vasodilators, antihyperlipemia agents, antitussives, bronchodilators, agents for peptic ulcers, gastroprokimetics, hormones, vitamins, hemostatics, agents for treatment of gout, antidiabetics, aldose reductase inhibitors, antineoplastics, antiallergic agents, antibiotics, synthetic antibacterials, antivirals, diagnostic agents, alkaloidal narcotics, and immunoregulatory drugs.

7. The lipid emulsion of claim 6 wherein the drug is selected from the group consisting of flurbiprofen, ibuprofen, indometacin, ketoprofen, diclofenac, pranoprofen, lidocaine, timolol, carteolol, pirenoxine, tropicamide, pilocarpine, naphazoline, phenylephrine, theophylline, prednisolone, betamethasone, dexamethasone, prostaglandin $E_1$, vitamin A, vitamin D, vitamin E, vitamin K, epalrestat, [5-(3-thienyl)-1H-tetrazol-1-yl] acetic acid, tegafur, fluorouracil, doxorubicin, mitomycin C, cisplatin, adriamycin, diphenhydramine, chlorpheniramine, glycyrrhizin, tazanolast, tranilast, ketotifen, 3'-(1H-tetrazol-5-yl)oxanilic acid, amphotericin B, erythromycin, chloramphenicol, cefixime, miconazole, pimaricin, norfloxacin, ofloxacin, levofloxacin, ciclosporin, glycyrrhetic acid, fluorometholone, diazepam, cimetidine, carbazochrome, fluorescein, morphine, sulpiride, tolazoline, papaverine, denopamine, frosemide, diltiazem, nicardipine, pravastatin, methylephedrine, trimebutine, allopurinol, tolbutamide, propyliodone, amogastrin, aciclovir and derivatives thereof.

8. A pharmaceutical preparation in the form of an injection, an eye drop, a nasal drop, a lotion, a liniment, an inhalant or a drug for oral administration which comprises the lipid emulsion according to claim 1.

* * * * *